(12) United States Patent
Sievernich et al.

(10) Patent No.: US 9,253,984 B2
(45) Date of Patent: Feb. 9, 2016

(54) HERBICIDAL COMPOSITIONS COMPRISING PYROXASULFONE VII

(75) Inventors: Bernd Sievernich, Hassloch (DE); Anja Simon, Weinheim (DE); William Karl Moberg, Hassloch (DE); Richard R. Evans, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 165 days.

(21) Appl. No.: 12/922,188

(22) PCT Filed: Mar. 13, 2009

(86) PCT No.: PCT/EP2009/052989
§ 371 (c)(1),
(2), (4) Date: Sep. 13, 2010

(87) PCT Pub. No.: WO2009/112572
PCT Pub. Date: Sep. 17, 2009

(65) Prior Publication Data
US 2011/0021356 A1     Jan. 27, 2011

Related U.S. Application Data

(60) Provisional application No. 61/036,580, filed on Mar. 14, 2008.

(51) Int. Cl.
*A01N 43/80* (2006.01)
*A01N 37/40* (2006.01)
*A01N 37/08* (2006.01)

(52) U.S. Cl.
CPC .............. *A01N 43/80* (2013.01); *A01N 37/08* (2013.01); *A01N 37/40* (2013.01)

(58) Field of Classification Search
CPC .............................. A01N 43/80; A01N 37/40
USPC .......................................................... 504/130
See application file for complete search history.

(56) References Cited

U.S. PATENT DOCUMENTS

| 2005/0256004 A1 | 11/2005 | Takahashi et al. |
| 2007/0015662 A1 | 1/2007 | Rosinger et al. |
| 2008/0153704 A1 | 6/2008 | Yamaji et al. |
| 2011/0009265 A1 | 1/2011 | Sievernich et al. |
| 2011/0009266 A1 | 1/2011 | Sievernich et al. |
| 2011/0015067 A1 | 1/2011 | Sievernich et al. |
| 2011/0015068 A1 | 1/2011 | Sievernich et al. |
| 2011/0015069 A1 | 1/2011 | Sievernich et al. |
| 2011/0028325 A1 | 2/2011 | Sievernich et al. |
| 2011/0065579 A1 | 3/2011 | Sievernich et al. |

FOREIGN PATENT DOCUMENTS

| EP | 1 364 946 | 11/2003 |
| WO | WO 2005/104848 | 11/2005 |
| WO | WO 2006/097322 | 9/2006 |
| WO | WO 2006/097509 | 9/2006 |
| WO | WO 2007/006409 | 1/2007 |
| WO | WO 2008/075743 | 6/2008 |
| WO | WO 2009/141367 | 11/2009 |

OTHER PUBLICATIONS

Behnken, L., Evaluation of the performance of KIH-485 for weed control in field corn in Potsdam, MN in 2004, 2004,NCWSS Research Report, V.61, pp. 94-95.*
Grossman, K., On the mechanism of selectivity of the corn herbicide BAS 662H: a combination of the novel auxin transport inhibitor diflufenzopyr and the auxin herbicide dicamba, 2002, Pest Management Science, vol. 58, pp. 1002-1014.*
Y. Yamaji et al., Application timing and field performance of KIH-485, Conference Abstract I-1-ii-12B of 11. IUPAC International Congress of Pesticide Chemistry, 2006 Kobe, Japan.
International Search Report for International Application No. PCT/EP2009/052989, Sep. 14, 2010.
International Preliminary Report on Patentability for International Application No. PCT/EP2009/052989, Sep. 14, 2010.

* cited by examiner

*Primary Examiner* — John Pak
*Assistant Examiner* — Andriae M Holt
(74) *Attorney, Agent, or Firm* — Brinks Gilson & Lione

(57) ABSTRACT

The present invention relates to herbicidally active compositions, which comprise 3-[5-(difluoromethoxy)-1-methyl-3-(trifluoromethyl)pyrazol-4-ylmethylsulfonyl]-4,5-dihydro-5,5-dimethyl-1,2-oxazole [common name pyroxasulfone] and at least one herbicide B and at least one herbicide B which is selected from group consisting of synthetic auxins and auxin transport inhibitors.
The invention furthermore relates to a method for controlling undesirable vegetation, which comprises applying an herbicidal composition according to the present invention to the undesirable plants. Application can be done before, during and/or after, preferably during and/or after, the emergence of the undesirable plants. The herbicide A and the at least one herbicide B can be applied simultaneously or in succession.

5 Claims, No Drawings

HERBICIDAL COMPOSITIONS COMPRISING PYROXASULFONE VII

This application is a National Stage application of International Application No. PCT/EP2009/052989 filed Mar. 13, 2009, which claims the benefit of U.S. Provisional Application No. 61/036,580, filed Mar. 14, 2008, the entire contents of which are hereby incorporated herein by reference.

The present invention relates to herbicidally active compositions, which comprise 3-[5-(difluoromethoxy)-1-methyl-3-(trifluoromethyl)pyrazol-4-ylmethylsulfonyl]-4,5-dihydro-5,5-dimethyl-1,2-oxazole [common name pyroxasulfone] and at least one herbicide B.

BACKGROUND OF THE INVENTION

In crop protection, it is desirable in principle to increase the specificity and the reliability of the action of active compounds. In particular, it is desirable for the crop protection product to control the harmful plants effectively and, at the same time, to be tolerated by the useful plants in question.

Pyroxasulfone has been described in EP-A 1364946 and US 2005/0256004.

Although pyroxasulfone is a highly effective pre-emergence herbicide, its activity at low application rates is not always satisfactory. Moreover, pyroxasulfone is known to have only poor post-emergence activity (Y. Yamaji et al., "Application timing and field performance of KIH-485", Conference Abstract I-1-ii-12B of 11. IUPAC International Congress of Pesticide Chemistry, 2006 Kobe, Japan). Apart from that, its compatibility with certain dicotyledonous crop plants such as cotton, sunflower, soybean, brassica crops such as canola and oilseed rape and some graminaceous plants such as rice, wheat, rye and barley is not always satisfactory, i.e. in addition to the harmful plants, the crop plants are also damaged to an extent which is not acceptable. Though it is in principle possible to spare crop plants by lowering the application rates, the extent of the control of harmful plants is naturally also reduced.

It is known that combined application of certain different herbicides with specific action might result in an enhanced activity of a herbicide component in comparison with a simple additive action. Such an enhanced activity is also termed a synergism or synergistic activity. As a consequence, it is possible to reduce the application rates of herbicidally active compounds required for controlling the harmful plants.

WO 2005/104848 describes compositions containing a herbicidal 3-sulfonylisoxazoline compound such as pyroxasulfone and a herbicide-antagonistically active amount of a safener. Similar compositions are known from WO 2007/006509.

US 2005/256004, for example, discloses that in a pre-emergence treatment, joint application of certain herbicidal 3-sulfonylisoxazoline compounds such as pyroxasulfone with atrazine or cyanazine results in an increased overall herbicide action against certain monocotyledonous and dicotyledonous annual broadleaf weeds (lambsquarter, green foxtail, velvetleaf) in comparison with a simple expected additive action.

WO 2006/097322 discloses a herbicidal composition comprising pyroxasulfone and a second herbicide selected from tembotrione, topramezone and 4-hydroxy-3-[[2-[(2-methoxyethoxy)methyl]-6-(trifluoromethyl-3-pyridinyl]carbonyl]bicyclo[3.2.1]oct-3-ene-2-one.

WO 2006/097509 discloses a herbicidal composition comprising a herbicidal 3-sulfonylisoxazoline compound such as pyroxasulfone and a phenyluracil compound.

Unfortunately, it is usually not possible to predict synergistic activity for combinations of known herbicides, even if the compounds show a close structural similarity to known synergistic combinations.

SUMMARY OF THE INVENTION

It is an object of the present invention to provide herbicidal compositions, which show enhanced herbicide action in comparison with the herbicide action of pyroxasulfone against undesirable harmful plants, in particular against *Alopecurus myosuroides, Avena fatua, Bromus* spec., *Echinocloa* spec., *Lolium* spec., *Phalaris* spec., *Setaria* spec., *Digitaria* spec., *Brachiaria* spec., *Amaranthus* spec., *Chenopodium* spec., *Abutilon theophrasti, Galium aparine, Veronica* spec., or *Solanum* spec. and/or to improve their compatibility with crop plants, in particular improved compatibility with wheat, barley, rye, rice, soybean, sunflower, *brassica* crops and/or cotton. The composition should also have a good herbicidal activity in post-emergence applications. The compositions should also show an accelerated action on harmful plants, i.e. they should effect damaging of the harmful plants more quickly in comparison with application of the individual herbicides.

We have found that this object is achieved, surprisingly, by herbicidally active compositions comprising
a) pyroxasulfone, i.e. 3-[5-(difluoromethoxy)-1-methyl-3-(trifluoromethyl)pyrazol-4-ylmethylsulfonyl]-4,5-dihydro-5,5-dimethyl-1,2-oxazole (hereinafter also referred to as herbicide A);
and
b) at least one herbicide B which is selected from group consisting of synthetic auxins and auxin transport inhibitors.

The invention relates in particular to compositions in the form of herbicidally active compositions as defined above.

The invention also relates to the use of a composition as defined herein for controlling undesirable vegetation. When using the compositions of the invention for this purpose the herbicide A and the at least one herbicide B can be applied simultaneously or in succession, where undesirable vegetation may occur.

The invention furthermore relates to the use of a composition as defined herein for controlling undesirable vegetation in crops. When using the compositions of the invention for this purpose the herbicide A and the at least one herbicide B can be applied simultaneously or in succession in crops, where undesirable vegetation may occur.

The invention furthermore relates to the use of a composition as defined herein for controlling undesirable vegetation in crops which, by genetic engineering or by breeding, are resistant and/or tolerant to one or more herbicides and/or pathogens such as harmful fungi, and/or to attack by insects; preferably resistant and/or tolerant to one or more synthetic auxin herbicides or auxin transport inhibitor herbicides.

The invention furthermore relates to a method for controlling undesirable vegetation, which comprises applying an herbicidal composition according to the present invention to the undesirable plants. Application can be done before, during and/or after, preferably during and/or after, the emergence of the undesirable plants. The herbicide A and the at least one herbicide B can be applied simultaneously or in succession.

The invention in particular relates to a method for controlling undesirable vegetation in crops, which comprises applying an herbicidal composition according to the present invention in crops where undesirable vegetation occurs or might occur.

The invention furthermore relates to a method for controlling undesirable vegetation, which comprises allowing a composition according to the present invention to act on plants, their habitat or on seed.

In the uses and methods of the present invention it is immaterial whether the herbicide A and the at least one herbicide B are formulated and applied jointly or separately, and, in the case of separate application, in which order the application takes place. It is only necessary, that the herbicide A and the at least one herbicide B are applied in a time frame, which allows simultaneous action of the active ingredients on the plants.

The invention also relates to a herbicide formulation, which comprises a herbicidally active composition as defined herein and at least one carrier material, including liquid and/or solid carrier materials.

DETAILED DESCRIPTION OF THE INVENTION

Surprisingly, the compositions according to the invention have better herbicidal activity against harmful plants than would have been expected by the herbicidal activity of the individual compounds. In other words, the joint action of pyroxasulfone and the at least one herbicide B results in an enhanced activity against harmful plants in the sense of a synergy effect (synergism). For this reason, the compositions can, based on the individual components, be used at lower application rates to achieve a herbicidal effect comparable to the individual components. Moreover, the compositions of the present invention provide good post-emergence herbicidal activity, i.e. the compositions are particularly useful for combating/controlling harmful plants after their emergence. Apart form that, the compositions of the present invention show good crop compatibility, i.e. their use in crops leads to a reduced damage of the crop plants and/or does not result in increased damage of the crop plants.

As used herein, the terms "controlling" and "combating" are synonyms.

As used herein, the terms "undesirable vegetation" and "harmful plants" are synonyms.

The compositions of the invention comprise pyroxasulfone as a first component a).

As a second component b), the compositions of the invention comprise at least one herbicide B which is a synthetic auxin or an auxin transport inhibitor. Synthetic auxins are compounds which act like the phytohormones auxins such indole-3-acetic acid. Synthetic auxins belong to the group O of the HRAC classification system. Auxin transport inhibitor are compounds, which block the process of auxin transport by inhibition of the auxin efflux carrier complex and which belong to the group P of the HRAC classification system (see HRAC, Classification of Herbicides According to Mode of Action, http://www.plantprotection.org/hrac/MOA.html).

Herbicide compounds belonging to the group of synthetic auxins include e.g.
b.1 benzoic acid herbicides;
b.2 quinolinecarboxylic acid herbicides;
b.3 pyridine carboxylic acid herbicides;
b.4 phenoxycarboxylic acid herbicides;

Herbicide compounds belonging to the group of auxin transport inhibitor herbicides include e.g. diflufenzopyr and its salts.

Benzoic acid herbicides herbicides (b.1) include e.g. dicamba, tricamba, chloramben and 2,3,6-TBA (2,3,6-trichlorobenzoic acid) and the salts and esters thereof.

Quinolinecarboxylic acid herbicides herbicides (b.2) include e.g. quinclorac and quinmerac and the salts and esters thereof.

Pyridinecarboxylic acid herbicides herbicides (b.3) include e.g. aminopyralid, clopyralid, picloram, triclopyr and fluroxypyr and their salts and their esters.

Phenoxycarboxylic acid herbicides (b4) include, e.g. phenoxyacetic acid herbicides such as 2,4-D ((2,4-dichlorophenoxy)acetic acid), 3,4-DA ((3,4-dichlorophenoxy)acetic acid), MCPA (4-chloro-o-tolyloxyacetic acid), 2,4,5-T ((2,4,5-trichlorophenoxy)acetic acid), phenoxypropionic acid herbicides such as 2,4-DP (dichlorprop; 2-(2,4-dichlorophenoxy)propionic acid), 2,4-DP-P((R)-2-(2,4-dichlorophenoxy)propionic acid), 4-CPP (2-(4-chlorophenoxy)propionic acid), 3,4-DP (2-(3,4-dichlorophenoxy)propionic acid), fenoprop (2-(2,4,5-trichlorophenoxy)propionic acid), CMPP (mecoprop; 2-(4-chloro-o-tolyloxy)propionic acid), CMPP-P ((R)-2-(4-chloro-o-tolyloxy)propionic acid), and phenoxybutyric acid herbicides such as 4-CPB (4-(4-chlorophenoxy)butyric acid), 2,4-DB (4-(2,4-dichlorophenoxy)butyric acid), 3,4-DB (4-(3,4-dichlorophenoxy)butyric acid), 2,4,5-TB (4-(2,4,5-trichlorophenoxy)butyric acid), MCPB (4-(4-chloro-o-tolyloxy)butyric acid), their salts and their esters. Preferred phenoxycarboxylic acid herbicides (b4) include 2,4-D, MCPA, 2,4-DP (dichlorprop), 2,4-DP-P, CMPP (mecoprop), CMPP-P, MCPB, their salts and their esters In the compositions of the present invention the relative weight ratio of pyroxasulfone to herbicide B is preferably in the range from 1:500 to 500:1, in particular in the range from 1:250 to 250:1 and more preferably from 100:1 to 1:100. Accordingly, in the methods and uses of the invention, pyroxasulfone and the at least one herbicide B are applied within these weight ratios.

The compositions of the invention may also comprise, as a component c), one or more safeners. Safeners, also termed as herbicide safeners, are organic compounds which in some cases lead to better crop plant compatibility when applied jointly with specifically acting herbicides. Some safeners are themselves herbicidally active. In these cases, the safeners act as antidote or antagonist in the crop plants and thus reduce or even prevent damage to the crop plants. However, in the compositions of the present invention, safeners are generally not required. Therefore, a preferred embodiment of the invention relates to compositions which contain no safener or virtually no safener (i.e. less than 1% by weight, based on the total amount of herbicide A and herbicide B).

Suitable safeners, which can be used in the compositions according to the present invention, are known in the art, e.g. from The Compendium of Pesticide Common Names (http://www.alanwood.net/pesticides/);

Farm Chemicals Handbook 2000 Vol. 86, Meister Publishing Company, 2000;

B. Hock, C. Fedtke, R. R. Schmidt, Herbizide, Georg Thieme Verlag, Stuttgart 1995;

W. H. Ahrens, Herbicide Handbook, 7th Edition, Weed Science Society of America, 1994; and K. K. Hatzios, Herbicide Handbook, Supplement to 7th Edition, Weed Science Society of America, 1998.

Safeners include e.g. benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloracetyl)-1,3-oxazolidine, 4-(dichloroacetyl)-1-oxa-4-azaspiro[4.5]decane and oxabetrinil, as well as thereof agriculturally acceptable salts and, provided they have a carboxyl group, their agriculturally acceptable derivatives. 2,2,5-Trimethyl-3-(dichloroacetyl)-1,3-oxazolidine [CAS No. 52836-31-4] is also known under the name R-29148.4-(Dichloroacetyl)-1-oxa-4-azaspiro[4.5]decane [CAS No. 71526-07-03] is also known under the names AD-67 and MON 4660.

As a safener, the compositions according to the invention particularly preferably comprise at least one of the compounds selected from the group of benoxacor, cloquintocet, cyprosulfamide, dichlormid, fenchlorazole, fenclorim, fluxofenim, furilazole, isoxadifen, mefenpyr, naphthalic anhydride, 2,2,5-trimethyl-3-(dichloroacetyl)-1,3-oxazolidine, and 4-(dichloroacetyl)-1-oxa-4-azaspiro[4.5]decane and oxabetrinil; and the agriculturally acceptable salt thereof and, in the case of compounds having a COOH group, an agriculturally acceptable derivative as defined below.

A preferred embodiment of the invention relates to compositions which contain no safener or virtually no safener (i.e. less than 1% by weight, based on the total amount of herbicide A and the at least one herbicide B is applied).

The compositions of the invention may also comprise, as a component d), one or more herbicides D) which are different from the herbicides A and B. Such further herbicides D may broaden the activity spectrum of the inventive compositions. However, further herbicides D are generally not required. Therefore, a preferred embodiment of the invention relates to compositions which contain no further herbicide D or virtually no further herbicide D (i.e. less than 1% by weight, based on the total amount of herbicide A and herbicide B).

In particular, the compositions of the present invention consist of the herbicide A and the at least one herbicide B, i.e. they neither contain a safener nor a further herbicide D.

If the compounds of herbicide compounds mentioned as herbicides B, herbicides D and safeners (see below) have functional groups, which can be ionized, they can also be used in the form of their agriculturally acceptable salts. In general, the salts of those cations are suitable whose cations have no adverse effect on the action of the active compounds ("agricultural acceptable").

In general, the salts of those cations are suitable whose cations have no adverse effect on the action of the active compounds ("agricultural acceptable"). Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium (hereinafter also termed as organoammonium) in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, pentylammonium, hexylammonium, heptylammonium, 2-hydroxyethylammonium (olamine salts), 2-(2-hydroxyethoxy)eth-1-ylammonium (diglycolamine salts), di(2-hydroxyeth-1-yl)ammonium (diolamine salts), tri(2-hydroxyethyl)ammonium (trolamine salts), tris(3-propanol)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

In the compositions according to the invention, the compounds that carry a carboxyl group can also be employed in the form of agriculturally acceptable derivatives, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester. Preferred derivatives are the esters.

The compositions of the present invention are suitable for controlling a large number of harmful plants, including monocotyledonous weeds, in particular annual weeds such as gramineous weeds (grasses) including *Echinochloa* species such as barnyardgrass (*Echinochloa crusgalli* var. *crus-galli*), *Digitaria* species such as crabgrass (*Digitaria sanguinalis*), *Setaria* species such as green foxtail (*Setaria viridis*) and giant foxtail (*Setaria faberii*), *Sorghum* species such as johnsongrass (*Sorghum halepense* Pers.), *Avena* species such as wild oats (*Avena fatua*), *Cenchrus* species such as *Cenchrus echinatus, Bromus* species, *Lolium* species, *Phalaris* species, *Eriochloa* species, *Panicum* species, *Brachiaria* species, annual bluegrass (*Poa annua*), blackgrass (*Alopecurus myosuroides*), *Aegilops cylindrica*, *Agropyron repens*, *Apera spica-venti*, *Eleusine indica*, *Cynodon dactylon* and the like.

The compositions of the present invention are also suitable for controlling a large number of dicotyledonous weeds, in particular broad leaf weeds including *Polygonum* species such as wild buckwheat (*Polygonum convolvolus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, *Cassia* species, *Commelina* species, *Datura* species, *Euphorbia* species, *Geranium* species, *Galinsoga* species, morning-glory (*Ipomoea* species), *Lamium* species, *Malva* species, *Matricaria* species, *Sysimbrium* species, *Solanum* species, *Xanthium* species, *Veronica* species, *Viola* species, common chickweed (*Stellaria media*), velvetleaf (*Abutilon theophrasti*), Hemp sesbania (*Sesbania exaltata* Cory), *Anoda cristata*, *Bidens pilosa*, *Brassica kaber*, *Capsella bursa-pastoris*, *Centaurea cyanus*, *Galeopsis tetrahit*, *Galium aparine*, *Helianthus annuus*, *Desmodium tortuosum*, *Kochia scoparia*, *Mercurialis annua*, *Myosotis arvensis*, *Papaver rhoeas*, *Raphanus raphanistrum*, *Salsola kali*, *Sinapis arvensis*, *Sonchus arvensis*, *Thlaspi arvense*, *Tagetes minuta*, *Richardia brasiliensis*, and the like.

The compositions of the present invention are also suitable for controlling a large number of annual and perennial sedge weeds including *cyperus* species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

The compositions according to the present invention are suitable for combating/controlling common harmful plants in useful plants (i.e. in crops). The compositions of the present invention are generally suitable for combating/controlling undesired vegetation in Grain crops, including e.g.
- cereals (small grain cereals) such as wheat (*Triticum aestivum*) and wheat like crops such as durum (*T. durum*), einkorn (*T. monococcum*), emmer (*T. dicoccon*) and spelt (*T. spelta*), rye (*Secale cereale*), triticale (*Tritiosecale*), barley (*Hordeum vulgare*);
- maize (corn; *Zea mays*);
- sorghum (e.g. *Sorghum bicolour*);
- rice (*Oryza* spp. such as *Oryza sativa* and *Oryza glaberrima*); and
- sugar cane;

Legumes (*Fabaceae*), including e.g. soybeans (*Glycine max.*), peanuts (*Arachis hypogaea* and pulse crops such as peas including *Pisum sativum*, pigeon pea and cowpea, beans including broad beans (*Vicia faba*), *Vigna* spp., and *Phaseolus* spp. and lentils (*lens culinaris* var.);

brassicaceae, including e.g. canola (*Brassica napus*), oilseed rape (*Brassica napus*), cabbage (*B. oleracea* var.), mustard such as *B. juncea, B. campestris, B. narinosai, B. nigra* and *B. tournefortii*, and turnip (*Brassica rapa* var.);

other broadleaf crops including e.g. sunflower, cotton, flax, linseed, sugarbeet, potato and tomato;

TNV-crops (TNV: trees, nuts and vine) including e.g. grapes, citrus, pomefruit, e.g. apple and pear, coffee, pistachio and oilpalm, stonefruit, e.g. peach, almond, walnut, olive, cherry, plum and apricot;

turf, pasture and rangeland;

onion and garlic;

bulb ornamentals such as tulips and narcissus;

conifers and deciduous trees such as *pinus*, fir, oak, maple, dogwood, hawthorne, crabapple, and rhamnus (buckthorn); and garden ornamentals such as roses, petunia, marigold and snapdragon.

The compositions of the present invention are in particular suitable for combating/controlling undesired vegetation in wheat, barley, rye, triticale, *durum*, rice, corn, sugarcane, *sorghum*, soybean, pulse crops such as pea, bean and lentils, peanut, sunflower, sugarbeet, potato, cotton, *brassica* crops, such as oilseed rape, canola, mustard, cabbage and turnip, turf, pasture, rangeland, grapes, pomefruit, such as apple and pear, stonefruit, such as peach, almond, walnut, olive, cherry, plum and apricot, citrus, coffee, pistachio, garden ornamentals, such as roses, petunia, marigold, snap dragon, bulb ornamentals such as tulips and narcissus, conifers and deciduous trees such as *pinus*, fir, oak, maple, dogwood, hawthorne, crabapple and rhamnus.

The compositions of the present invention are most suitable for combating/controlling undesired vegetation in wheat, barley, rye, triticale, *durum*, rice, corn, sugarcane, sugarbeet, *sorghum*, soybean, pulse crops such as pea, bean and lentils, peanut, sunflower, potato, cotton, *brassica* crops, such as oilseed rape, canola, mustard, cabbage and turnip, turf, pasture, rangeland, grapes, stonefruit, such as peach, almond, walnut, olive, cherry, plum and apricot, citrus and pistachio.

If not stated otherwise, the compositions of the invention are suitable for application in any variety of the aforementioned crop plants.

The compositions of the invention are particularly suitable for application in wheat, barley, rye, triticale, *durum*, rice, corn, sugarcane, *sorghum*, pulse crops, sugarbeet, *brassica* crops, turf, stonefruit, citrus, pistachio, pasture and rangeland.

The compositions according to the invention can also be used in crop plants which are resistant or tolerant to one or more herbicides owing to genetic engineering or breeding, which are resistant or tolerant to one or more pathogens such as plant pathogenous fungi owing to genetic engineering or breeding, or which are resistant or tolerant to attack by insects owing to genetic engineering or breeding. Suitable are for example crop plants, preferably corn, wheat, sunflower, rice, canola, oilseed rape, soybeans, cotton and sugarcane which are resistant or tolerant to synthetic auxins, or crop plants which, owing to introduction of the gene for Bt toxin by genetic modification, are resistant to attack by certain insects.

The compositions of the present invention can be applied in conventional manner by using techniques a skilled person is familiar with. Suitable techniques include spraying, atomizing, dusting, spreading or watering. The type of application depends on the intended purpose in a well known manner; in any case, the techniques should ensure the finest possible distribution of the active ingredients according to the invention.

The compositions can be applied pre- or post-emergence, i.e. before, during and/or after emergence of the undesirable plants. When the compositions are used in crops, they can be applied after seeding and before or after the emergence of the crop plants.

The compositions invention can, however, also be applied prior to seeding of the crop plants.

It is a particular benefit of the compositions according to the invention that they have a very good post-emergence herbicide activity, i.e. they show a good herbicidal activity against emerged undesirable plants. Thus, in a preferred embodiment of invention, the compositions are applied post-emergence, i.e. during and/or after, the emergence of the undesirable plants. It is particularly advantageous to apply the mixtures according to the invention post emergent when the undesirable plant starts with leaf development up to flowering. Since the composition show good crop tolerance, even when the crop has already emerged, they can be applied after seeding of the crop plants and in particular during or after the emergence of the crop plants.

In any case herbicide A and the at least one herbicide B and the optional further actives (safener C and herbicide D) can be applied simultaneously or in succession.

The compositions are applied to the plants mainly by spraying, in particular foliar spraying. Application can be carried out by customary spraying techniques using, for example, water as carrier and spray liquor rates of from about 10 to 2000 l/ha or 50 to 1000 l/ha (for example from 100 to 500 l/ha). Application of the herbicidal compositions by the low-volume and the ultra-low-volume method is possible, as is their application in the form of microgranules.

If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal mixtures or compositions according to the invention are preferably applied by foliar application.

Application may be effected, for example, by usual spraying techniques with water as the carrier, using amounts of spray mixture of approx. 50 to 1000 l/ha.

The required application rate of the composition of the pure active compounds, i.e. of pyroxasulfone, herbicide B and optionally safener or herbicide D depends on the density of the undesired vegetation, on the development stage of the plants, on the climatic conditions of the location where the composition is used and on the application method. In general, the application rate of the composition (total amount of pyroxasulfone, herbicide B and optional further actives) is from 15 to 5000 g/ha, preferably from 20 to 2500 g/ha of active substance.

The required application rates of pyroxasulfone are generally in the range from 1 g/ha to 500 g/ha and preferably in the range from 5 g/ha to 400 g/ha or from 10 g/ha to 300 g/ha of active substance.

The required application rates of the herbicide B (total amount of herbicide B) are generally in the range from 1 g/ha to 3000 g/ha and preferably in the range from 5 g/ha to 2000 g/ha or from 10 g/ha to 1500 g/ha of active substance.

The required application rates of the safener, if applied, are generally in the range from 1 g/ha to 5000 g/ha and preferably in the range from 2 g/ha to 5000 g/ha or from 5 g/ha to 5000 g/ha of active substance. Preferably no safener or virtually no safener is applied and thus the application rates are below 5 g/ha, in particular below 2 g/ha or below 1 g/ha.

According to a first embodiment of the invention, the component b) comprises at least one benzoic acid herbicide. Benzoic acid herbicides (group b.1) are known e.g. from C. D. S. Tomlin, "The Pesticide Manual", 13th Edition, BCPC (2003), and also from The Compendium of Pesticide Common Names, http://www.alanwood.net/pesticides/.

Preferred benzoic acid herbicides b.1 include dicamba, tricamba, chloramben and 2,3,6-TBA (2,3,6-trichlorobenzoic acid) and the salts the esters thereof, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyl-ethyl)ammonium, tri(hydroxyethyl)ammonium, hydroxypropylammonium, di(hydroxypropyl)ammonium and tri(hydroxypropyl)ammonium salts, their diglycolamine salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Suitable examples of such salts are dicamba-sodium, dicamba-potassium, dicamba-methylammonium, dicamba-isopropylammonium, dicamba-olamine, dicamba-diolamine, dicamba-trolamine, tricamba-sodium, tricamba-potassium, tricamba-methylammonium, tricamba-isopropylammonium, tricamba-olamine, tricamba-diolamine, tricamba-trolamine, chloramben-ammonium, chloramben-methylammonium, chloramben-sodium, chloramben-diolamine, 2,3,6-T-sodium, 2,3,6-dimethylammonium. Suitable examples of such esters are dicamba-methyl and chloramben-methyl.

In particular preferred compositions of this embodiment, the herbicide B comprises or in particular is dicamba or a salt thereof.

In this embodiment the relative weight ratio of pyroxasulfone and a benzoic acid herbicide is preferably from 1:250 to 250:1, in particular from 100:1 to 1:100.

The rate of application of pyroxasulfone is usually from 1 g/ha to 500 g/ha and preferably in the range from 5 g/ha to 400 g/ha or from 10 g/ha to 300 g/ha of active substance (a.s.).

The rate of application of the benzoic acid herbicides is usually 1 to 2000 g/ha, as a rule 5 to 1500 g/ha, preferably 10 to 1000 g/ha, of active substance (a.s.).

The compositions of this embodiment are particularly suitable for controlling mono- and dicotyledonous weeds and sedge weeds, in particular *Alopecurus myosuroides, Apera spica-venti, Avena fatua, Brachiaria* spec., *Bromus* spec., *Digitaria* spec., *Echinocloa* spec., *Eleusine* spec., *Lolium* spec., *Phalaris* spec., *Poa annua, Setaria* spec., *Abuthilon theophrasti, Amaranthus* spec., *Ambrosia* spec., *Cassia* spec., *Chenopodium* spec., *Convolvolus* spec., *Conyza* spec., *Euphorbia* spec., *Ipomoea* spec., *Kochia scoparia, Malva* spec., *Polygonum* spec., *Sida* spec., *Xanthium* spec. and *Commelina* spec.

The compositions of this embodiment are in particular suitable for combating undesired vegetation in grain crops, in particular wheat, barley, rye, triticale, *durum*, corn and sugarcane, rice, *sorghum*, turf, rangeland, pasture, grapes, stonefruit, such as peach, almond, walnut, olive, cherry, plum and apricot, citrus and pistachio.

The compositions of this embodiment are most suitable for application in wheat, corn, rice, sugarcane, turf, rangeland, pasture, stonefruit, citrus and pistachio.

If not stated otherwise, the compositions of this embodiment are suitable for application in any variety of the aforementioned crop plants.

The compositions of this embodiment can preferably be used in crops which tolerate and/or are resistant to the action of auxin herbicides, preferably in crops which tolerate and/or are resistant to the action of benzoic acid herbicides. The resistance and or tolerance to said herbicides may be achieved by conventional breeding and/or by genetic engineering methods. Crops which are tolerant or resistant to auxin herbicides (e.g. tolerant to benzoic acid herbicides) include crops of soybeans, corn or cotton.

According to a second embodiment of the invention, the component b) comprises at least one quinolinecarboxylic acid herbicide. Quinolinecarboxylic acid herbicides (group b.2) are known e.g. from C. D. S. Tomlin, "The Pesticide Manual", 13th Edition, BCPC (2003), and also from The Compendium of Pesticide Common Names, http://www.alanwood.net/pesticides/.

Preferred quinolinecarboxylic acid herbicides include quinclorac, quinmerac, their salts and their esters, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters.

In particular preferred compositions of this embodiment, the herbicide B comprises or in particular is quinclorac or a salt or ester thereof.

In other particular preferred compositions of this embodiment, the herbicide B comprises or in particular is quinmerac or a salt or ester thereof.

In this embodiment the relative weight ratio of pyroxasulfone and quinolinecarboxylic acid herbicides is preferably from 250:1 to 1:250, in particular from 100:1 to 1:100.

The rate of application of pyroxasulfone is usually from 1 g/ha to 500 g/ha and preferably in the range from 5 g/ha to 400 g/ha or from 10 g/ha to 300 g/ha of active substance (a.s.).

The rate of application of the quinolinecarboxylic acid herbicide is usually 1 to 1500 g/ha, as a rule 5 to 1000 g/ha, preferably 10 to 750 g/ha, of active substance (a.s.).

The compositions of this embodiment are particularly suitable for controlling mono- and dicotyledonous weeds and sedge weeds, in particular *Alopecurus myosuroides, Apera*

*spica-venti, Avena fatua, Brachiaria* spec., *Bromus* spec., *Digitaria* spec., *Echinocloa* spec., *Eleusine* spec., *Lolium* spec., *Phalaris* spec., *Poa annua, Setaria* spec., *Amaranthus* spec., *Chenopodium* spec., *Convolvolus* spec., *Euphorbia* spec., *Galium aparine, Ipomoea* spec. and *Solanum* spec.

The compositions of this embodiment are in particular suitable for combating undesired vegetation in wheat, barley, rye, triticale, *durum*, rice, corn, sugarcane, *sorghum*, soybean, pulse crops such as pea, bean and lentils, peanut, *brassica*-crops such as oilseed rape, canola and mustard, sunflower, potato, cotton, grapes, stonefruit, such as peach, almond, walnut, olive, cherry, plum and apricot, citrus and pistachio.

The compositions of this embodiment are most suitable for application in wheat, barley, rye, *durum*, rice, corn, sugarcane, soybean, pulse crops, sugarbeet, *brassica* crops, turf, pasture and rangeland.

If not stated otherwise, the compositions of this embodiment are suitable for application in any variety of the aforementioned crop plants.

The compositions of this embodiment can preferably be used in crops which tolerate and/or are resistant to the action of auxin herbicides, preferably in crops which tolerate and/or are resistant to the action of quinolinecarboxylic acid herbicides. The resistance and or tolerance to said herbicides may be achieved by conventional breeding and/or by genetic engineering methods.

According to a third embodiment of the invention, the component b) comprises at least one pyridinecarboxylic acid herbicide. Pyridinecarboxylic acid herbicides (group b.3) are known e.g. from C. D. S. Tomlin, "The Pesticide Manual", 13th Edition, BCPC (2003), and also from The Compendium of Pesticide Common Names, http://www.alanwood.net/pesticides/.

Pyridinecarboxylic acid herbicides include aminopyralid, clopyralid, picloram, triclopyr and fluoroxypyr and their salts and their esters, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Suitable examples of such salts and esters are aminopyralid-potassium, aminopyralid-tris(2-hydroxypropyl)ammonium, clopyralid-potassium, clopyralid-olamine, clopyralid-tris(2-hydroxypropyl)ammonium, clopyralid-methyl, picloram-potassium, picloram-triethylammonium, picloram-tris(2-hydroxypropyl)ammonium, picloram-methyl, picloram-2-ethylhexyl, picloram-isooctyl, fluoroxypyr-meptyl, fluoroxypyrbutomethyl, triclopyr-triethylammonium, triclopyr-ethyl and triclopyr-butotyl.

In particular preferred compositions of this embodiment, the herbicide B comprises or in particular is fluoroxypyr or a salt or ester thereof.

In this embodiment the relative weight ratio of pyroxasulfone and pyridinecarboxylic acid herbicide is preferably from 250:1 to 1:250, in particular from 100:1 to 1:100.

The rate of application of pyroxasulfone is usually from 1 g/ha to 500 g/ha and preferably in the range from 5 g/ha to 400 g/ha or from 10 g/ha to 300 g/ha of active substance (a.s.).

The rate of application of the pyridinecarboxylic acid herbicide is usually 1 to 2000 g/ha, preferably 5 to 1500 g/ha, in particular 10 to 1000 g/ha of active substance (a.s.).

The compositions of this embodiment are particularly suitable for controlling mono- and dicotyledonous weeds and sedge weeds, in particular *Alopecurus myosuroides, Apera spica-venti, Avena fatua, Brachiaria* spec., *Bromus* spec., *Digitaria* spec., *Echinocloa* spec., *Eleusine* spec., *Lolium* spec., *Phalaris* spec., *Poa annua, Setaria* spec., *Anthemis* spec., *Centaurea cyanus, Cirsium* spec., *Convolvolus* spec., *Galium aparine, Ipomoea* spec., *Kochia scoparia, Matricaria* spec. and *Polygonum*.

The compositions of this embodiment are in particular suitable for combating undesired vegetation in wheat, barley, rye, triticale, *durum*, rice, corn, sugarcane, *sorghum*, sugarbeet, *brassica*-crops such as oilseed rape, canola and mustard, grapes, stonefruit, such as peach, almond, walnut, olive, cherry, plum and apricot, turf, pasture, rangeland, citrus and pistachio.

The compositions of this embodiment are most suitable for application in wheat, barley, corn, sugarcane, *brassica* crops, sugarbeet, turf, pasture and rangeland.

If not stated otherwise, the compositions of this embodiment are suitable for application in any variety of the aforementioned crop plants.

The compositions of this embodiment can preferably be used in crops which tolerate and/or are resistant to the action of auxin herbicides, preferably in crops which tolerate and/or are resistant to the action of pyridinecarboxylic acid herbicides. The resistance and or tolerance to said herbicides may be achieved by conventional breeding and/or by genetic engineering methods. Crops which are tolerant or resistant to auxin herbicides (e.g. tolerant or resistant to pyridinecarboxylic acid herbicides) include crops of soybeans, corn, cotton, rice, canola and oilseed rape.

According to a forth embodiment of the invention, the component b) comprises at least one phenoxycarboxylic acid herbicide. Phenoxycarboxylic herbicides (group b.4) are known e.g. from C. D. S. Tomlin, "The Pesticide Manual", 13th Edition, BCPC (2003), and also from The Compendium of Pesticide Common Names, http://www.alanwood.net/pesticides/.

Preferred phenoxycarboxylic acid herbicides include 2,4-D, 2,4-DP (dichlorprop), 2,4-DP-P, CMPP (mecoprop), CMPP-P, MCPA, MCPB, their salts and their esters, in particular their sodium salt, potassium salt, ammonium salt or substituted ammonium salts as defined above, in particular mono-, di- and tri-$C_1$-$C_8$-alkylammonium salts such as methylammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts and their esters, in particular its $C_1$-$C_8$-alkyl esters and $C_1$-$C_4$-alkoxy-$C_2$-$C_4$-alkyl esters, such as methylesters, ethylesters, iso-propyl, butyl, hexyl, heptyl, iso-heptyl, isooctyl, 2-ethylhexyl and butoxyethyl esters. Suitable examples of such salts and esters are When this substance is used as an ester or a salt, its identity should be stated, for example 2,4-Dammonium, 2,4-D-butotyl, 2,4-D-2-butoxypropyl, 2,4-D-3-butoxypropyl, 2,4-D-butyl, 2,4-D-diethylammonium, 2,4-D-dimethylammonium, 2,4-D-diolamine, 2,4-Ddodecylammonium, 2,4-D-ethyl, 2,4-D-2-ethylhexyl, 2,4-D-heptylammonium, 2,4-Disobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-Dtefuryl, 2,4-D- tetradecylammonium, 2,4-D-triethylammonium, 2,4-D-tris (2-hydroxypropyl)ammonium, 2,4-D-trolamine, MCPA-butotyl, MCPA-butyl, MCPAdimethylammonium, MCPA-diolamine, MCPA-ethyl, MCPA-2-ethylhexyl, MCPAisobutyl, MCPA-isoctyl, MCPA-isopropyl, MCPA-methyl, MCPA-olamine, MCPApotassium, MCPA-sodium, MCPA-trolamine, dichlorprop-butotyl, dichlorpropdimethylammonium, dichlorprop-ethylammonium, dichlorprop-2-ethylhexyl, dichlorpropisoctyl, dichlorprop-methyl, dichlorprop-potassium, dichlorprop-sodium, dicloprop-P-dimethylammonium, mecoprop-dimethylammonium, mecoprop-diolamine, mecopropethadyl, mecoprop-isoctyl, mecoprop-methyl, mecoprop-potassium, mecoprop-sodium, mecoprop-trolamine, mecoprop-P-dimethylammonium, mecoprop-P-isobutyl, mecoprop-P-potassium, MCPB-methyl, MCPB-ethyl and MCPB-sodium.

In particular preferred compositions of this embodiment, the herbicide B comprises or in particular is 2,4-D or a salt or ester thereof.

In particular preferred compositions of this embodiment, the herbicide B comprises or in particular is MCPA or a salt or ester thereof.

In particular preferred compositions of this embodiment, the herbicide B comprises or in particular is dicloprop, dicloprop-P or a salt or ester thereof.

In particular preferred compositions of this embodiment, the herbicide B comprises or in particular is mecoprop, mecoprop-P or a salt or ester thereof.

In particular preferred compositions of this embodiment, the herbicide B comprises or in particular is MCPB or a salt or ester thereof.

In this embodiment the relative weight ratio of pyroxasulfone and phenoxycarboxylic acid herbicide is preferably from 500:1 to 1:500, in particular from 250:1 to 1:250.

The rate of application of pyroxasulfone is usually from 1 g/ha to 500 g/ha and preferably in the range from 5 g/ha to 400 g/ha or from 10 g/ha to 300 g/ha of active substance (a.s.).

The rate of application of the phenoxycarboxylic acid herbicide is usually 1 to 3000 g/ha, as a rule 5 to 2000 g/ha, preferably 10 to 1500 g/ha, of active substance (a.s.).

The compositions of this embodiment are particularly suitable for controlling mono- and dicotyledonous weeds and sedge weeds, in particular *Alopecurus myosuroides, Apera spica-venti, Avena fatua, Brachiaria* spec., *Bromus* spec., *Digitaria* spec., *Echinocloa* spec., *Eleusine* spec., *Lolium* spec., *Phalaris* spec., *Poa annua, Setaria* spec., *Amaranthus* spec., *Chenopodium* spec., *Cirsium* spec., *Convolvolus* spec., *Conyza* spec., *Galium aparine, Geranium* spec., *Ipomoea* spec., *Malva* spec., *Papaver rhoeas, Polygonum* spec., *Sonchus arvensis* and *Stellaria media*.

The compositions of this embodiment are in particular suitable for combating undesired vegetation in wheat, barley, rye, triticale, *durum*, rice, corn, sugarcane, *sorghum*, pulse crops such as pea, bean and lentils, turf, pasture, rangeland, TNV crops, such as grapes, stonefruit, such as peach, almond, walnut, olive, cherry, plum and apricot, citrus and pistachio.

The compositions of this embodiment are most suitable for application in wheat, barley, rice, corn, sugarcane, stonefruit, citrus, pistachio, turf, pasture and rangeland.

If not stated otherwise, the compositions of this embodiment are suitable for application in any variety of the aforementioned crop plants.

The compositions of this embodiment can preferably be used in crops which tolerate and/or are resistant to the action of auxin herbicides, preferably in crops which tolerate and/or are resistant to the action of phenoxycarboxylic acid herbicides. The resistance and or tolerance to said herbicides may be achieved by conventional breeding and/or by genetic engineering methods. Crops which are tolerant to auxin herbicides (e.g. tolerant to phenoxycarboxylic acid herbicides) include crops of soybeans, corn, cotton, rice, canola and oilseed rape.

According to a fifth embodiment of the invention, the component b) comprises at least one auxin-transport-inhibitor herbicide. Auxin-transport-inhibitor herbicide herbicides are known e.g. from C. D. S. Tomlin, "The Pesticide Manual", 13th Edition, BCPC (2003), and also from The Compendium of Pesticide Common Names, http://www.alanwood.net/pesticides/.

Auxin-transport-inhibitor herbicides include diflufenzopyr and naptalam. Also included are the salts of diflufenzopyr and naptalam, in particular their sodium salt, potassium salt, ammonium salt or substituted ammonium salts as defined above, in particular mono-, di- and tri-$C_1$-$C_8$-alkylammonium salts such as isopropylammonium salts. Suitable examples of such salts and esters are diflufenzopyr-sodium and naptalam sodium.

Preferred auxin-transport-inhibitor herbicide is diflufenzopyr and its salts as described above.

In this embodiment the relative weight ratio of pyroxasulfone and auxin-transport-inhibitor herbicide is preferably from 500:1 to 1:500, in particular from 250:1 to 1:250.

The rate of application of pyroxasulfone is usually from 1 g/ha to 500 g/ha and preferably in the range from 5 g/ha to 400 g/ha or from 10 g/ha to 300 g/ha of active substance (a.s.).

The rate of application of the auxin-transport-inhibitor herbicide is usually 0.1 to 1000 g/ha, as a rule 1 to 750 g/ha, preferably 5 to 500 g/ha, of active substance (a.s.).

The compositions of this embodiment are particularly suitable for controlling mono- and dicotyledonous weeds and sedge weeds, in particular *Alopecurus myosuroides, Apera spica-venti, Avena fatua, Brachiaria* spec., *Bromus* spec., *Digitaria* spec., *Echinocloa* spec., *Eleusine* spec., *Lolium* spec., *Phalaris* spec., *Poa annua, Setaria* spec., *Abuthilon theophrasti, Amaranthus* spec., *Chenopodium* spec., *Galium aparine, Ipomoea* spec., and *Polygonum* spec.

The compositions of this embodiment are in particular suitable for combating undesired vegetation in wheat, barley, rye, triticale, *durum*, rice, corn, sugarcane, *sorghum*, turf, pasture, rangeland, TNV crops, such as grapes, stonefruit, such as peach, almond, walnut, olive, cherry, plum and apricot, citrus and pistachio.

The compositions of this embodiment are most suitable for application in wheat, barley, rice, corn, sugarcane, turf, pasture, rangeland, stonefruit, citrus and pistachio.

If not stated otherwise, the compositions of this embodiment are suitable for application in any variety of the aforementioned crop plants.

The compositions of this embodiment can preferably be used in crops which tolerate and/or are resistant to the action of auxin-type or auxin-transport-inhibitor herbicides, preferably in crops which tolerate and/or are resistant to the action of diflufenzopyr or synthetic auxins. The resistance and or tolerance to said herbicides may be achieved by conventional breeding and/or by genetic engineering methods. Crops which are tolerant or resistant to synthetic auxins or auxin-transport-inhibitor herbicides (e.g. tolerant or resistant to diflufenzopyr) include crops of soybeans, corn, cotton, rice, canola and oilseed rape.

According to a sixth embodiment of the invention, the component b) comprises a mixture of at least one herbicide from the group of synthetic auxin herbicides and at least one auxin-transport-inhibitor herbicide, the latter being preferably diflufenzopyr or a salt thereof.

In this embodiment the at least one synthetic auxin herbicide is preferably selected from the herbicides of the groups b.1, b.2, b.3 and b.4, in particular selected from the groups of b.1: dicamba, tricamba, chloramben, 2,3,6-TBA (2,3,6-trichlorobenzoic acid) and the salts and esters thereof;
b.2: quinclorac and quinmerac and the salts and esters thereof;
b.3: aminopyralid, clopyralid, picloram, triclopyr and fluoroxypyr and their salts and their esters;
b.4: 2,4-D, 3,4-DA, MCPA, 2,4,5-T, 2,4-DP, 2,4-DP-P, 4-CPP, 3,4-DP, fenoprop, CMPP, CMPP-P, 4-CPB, 2,4-DB, 3,4-DB, 2,4,5-TB, MCPB, their salts and their esters.

In this embodiment the at least one synthetic auxin herbicide is more preferably selected from the herbicides of the groups b.1. in particular dicamba or a salt or ester thereof, as defined above.

In a particular preferred embodiment, the composition comprises pyroxasulfone, diflufenzopyr or a salt thereof and dicamba or a salt or ester thereof.

In this embodiment the relative weight ratio of pyroxasulfone and herbicide B, i.e. auxin-type herbicide+auxin-transport-inhibitor herbicide is preferably from 500:1 to 1:500, in particular from 250:1 to 1:250 and especially from 100:1 to 1:100.

In this embodiment the relative weight ratio of auxin-type herbicide to auxin-transport-inhibitor herbicide is preferably from 500:1 to 1:500, in particular from 250:1 to 1:250 and especially from 100:1 to 1:100.

The rate of application of pyroxasulfone is usually from 1 g/ha to 500 g/ha and preferably in the range from 5 g/ha to 400 g/ha or from 10 g/ha to 300 g/ha of active substance (a.s.).

The rate of application of auxin-type herbicide is usually 1 to 2000 g/ha, as a rule 5 to 1500 g/ha, preferably 10 to 1000 g/ha, of active substance (a.s.).

The rate of application of auxin-transport inhibitor herbicide is usually 0.1 to 1000 g/ha, as a rule 1 to 750 g/ha, preferably 5 to 500 g/ha, of active substance (a.s.).

The compositions of this embodiment are particularly suitable for controlling mono- and dicotyledonous weeds and sedge weeds, in particular *Alopecurus myosuroides, Apera spica-venti, Avena fatua, Brachiaria* spec., *Bromus* spec., *Digitaria* spec., *Echinocloa* spec., *Eleusine* spec., *Lolium* spec., *Phalaris* spec., *Poa annua, Setaria* spec., *Abuthilon theophrasti, Amaranthus* spec.,*Ambrosia* spec., *Cassia* spec., *Cirsium* spec., *Chenopodium* spec., *Convolvulus* spec., *Conyza* spec., *Euphorbia* spec., *Galium aparine, Ipomoea* spec., *Kochia scoparia, Malva* spec., *Polygonum* spec., *Sida* spec., *Xanthium* spec. and *Commelina* spec.

The compositions of this embodiment are in particular suitable for combating undesired vegetation in wheat, barley, rye, triticale, *durum*, rice, corn, *sorghum*, sugar cane, turf, rangeland, pasture, grapes, stonefruit, such as peach, almond, walnut, olive, cherry, plum and apricot, citrus and pistachio.

The compositions of this embodiment are most suitable for application in wheat, rice, corn, sugar cane, turf, rangeland, pasture, stonefruit, citrus and pistachio.

If not stated otherwise, the compositions of this embodiment are suitable for application in any variety of the aforementioned crop plants.

The present invention also relates to formulations of the compositions according to the present invention. The formulations contain, besides the composition, at least one organic or inorganic carrier material. The formulations may also contain, if desired, one or more surfactants and, if desired, one or more further auxiliaries customary for crop protection compositions.

The formulation may be in the form of a single package formulation containing both the herbicide A and the at least one herbicide B together with liquid and/or solid carrier materials, and, if desired, one or more surfactants and, if desired, one or more further auxiliaries customary for crop protection compositions. The formulation may be in the form of a two package formulation, wherein one package contains a formulation of pyroxasulfone while the other package contains a formulation of the at least one herbicide B and wherein both formulations contain at least one carrier material, if desired, one or more surfactants and, if desired, one or more further auxiliaries customary for crop protection compositions. In the case of two package formulations the formulation containing pyroxasulfone and the formulation containing the herbicide B are mixed prior to application. Preferably the mixing is performed as a tank mix, i.e. the formulations are mixed immediately prior or upon dilution with water. If the composition comprises one or more actives such as a second herbicide B, a safener C and/or a herbicide D, the composition may be formulated as a single package formulation but may also be formulated as a three or four package formulation.

In the formulation of the present invention the active ingredients, i.e. pyroxasulfone, herbicide B and optional further actives are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

Depending on the formulation type, they comprise one or more liquid or solid carriers, if appropriate surfactants (such as dispersants, protective colloids, emulsifiers, wetting agents and tackifiers), and if appropriate further auxiliaries which are customary for formulating crop protection products. The person skilled in the art is sufficiently familiar with the recipes for such formulations. Further auxiliaries include e.g. organic and inorganic thickeners, bactericides, antifreeze agents, antifoams, colorants and, for seed formulations, adhesives.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

To prepare emulsions, pastes or oil dispersions, the active the components, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Powders, materials for spreading and dusts can be prepared by mixing or concomitant grinding of the active the components a) and b) and optionally safener c) and/or herbicide D with a solid carrier.

Granules, e.g. coated granules, impregnated granules and homogeneous granules, can be prepared by binding the active ingredients to solid carriers.

The formulations of the invention comprise a herbicidally effective amount of the composition of the present invention. The concentrations of the active the active ingredients in the formulations can be varied within wide ranges. In general, the formulations comprise from 1 to 98% by weight, preferably 10 to 60% by weight, of active ingredients (sum of pyroxasulfone, herbicide B and optionally further actives). The active ingredients are employed in a purity of from 90% to 100%, preferably 95% to 100% (according to NMR spectrum).

The active compounds A and B and the optionally further actives as well as the compositions according to the invention can, for example, be formulated as follows:

1. Products for Dilution with Water

A Water-Soluble Concentrates 10 parts by weight of active compound (or composition) are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound (or composition) are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound (or composition) are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound (or composition) are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound (or composition) are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound (or composition) are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound (or composition) are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound (or composition), 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound (or composition) are ground finely and mixed intimately with 95 parts by weight of finely divided kaolin. This gives a dusting powder with an active compound content of 5% by weight.

J Granules (GR, FG, GG, MG)

0.5 parts by weight of active compound (or composition) are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound (or composition) are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

It may furthermore be beneficial to apply the compositions of the invention alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

Use Examples

The effect of the herbicidal compositions according to the invention of herbicides A and B and, if appropriate, safener on the growth of undesirable plants compared to the herbicidally active compounds alone was demonstrated by the following greenhouse experiments:

For the pre-emergence treatment, directly after sowing the active compounds, which had been suspended or emulsified in water, were applied by means of finely distributed nozzles. The containers were irrigated gently to promote germination and growth and subsequently covered with transparent plastic hoods until plant had rooted. This cover caused uniform germination of the tests plants, unless this was adversely affected by active compounds.

For the post-emergence treatment, the test plants were first grown to a height of 3 to 20 cm, depending on the plant habit, and only then treated. Here, the herbicidal compositions were suspended or emulsified in water as distribution medium and sprayed using finely distributing nozzles.

The respective herbicides A and/or safener were formulated as 10% by weight strength emulsion concentrate and introduced to the spray liquor with the amount of solvent system used for applying the active compound. In the examples, the solvent used was water. Herbicide B and/or safener were used as commercially available formulations and introduced to the spray liquor with the amount of solvent system used for applying the active compound. In the examples, the solvent used was water.

Dicamba was used as a commercial aqueous solution having an active ingredient concentration of 480 g/l.

The test period extended over 21 days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

The plants used in the greenhouse experiments belonged to the following species:

| Scientific Name | Code | Common Name |
|---|---|---|
| Abutilon theophrasti | ABUTH | velvetleaf |
| Agropyron repens | AGRRE | quackgrass |
| Alopecurus myosuroides | ALOMY | blackgrass |
| Amaranthus retroflexus | AMARE | pig weed |
| Ambrosia artemisifolia | AMBEL | common ragweed |
| Apera spica-venti | APESV | windgrass |
| Avena fatua | AVEFA | wild oat |
| Brachiaria plantaginea | BRAPL | alexandergrass |
| Bromus inermis | BROIN | awnless brome |
| Bromus sterilis | BROST | sterile brome |
| Brassica napus spp. napus | BRSNW | winter oilseed-rape |
| Capsella bursa-pastoris | CAPBP | sheperd's-purse |
| Cenchrus echinatus | CCHEC | sandbur |
| Chenopodium album | CHEAL | lambsquarter |
| Commelina benghalensis | COMBE | tropical spiderwort |
| Digitaria sanguinalis | DIGSA | large crabgrass |
| Echinochloa crus-galli | ECHCG | barnyardgrass |
| Eleusine indica | ELEIN | goosegrass |
| Galium aparine | GALAP | cleaver |
| Glycine max | GLXMA | soybean |
| Gossypium hirsutum | GOSHI | cotton |
| Helianthus annuus | HELAN | sunflower |
| Hordeum vulgare | HORVW | winter barley |
| Kochia scoparia | KCHSC | kochia |
| Lamium purpureum | LAMPU | red deadnettle |
| Lolium multiflorum | LOLMU | italian ryegrass |
| Matricaria inermis | MATIN | scentless mayweed |
| Mercurialis annua | MERAN | annual mercury |
| Orysa sativa | ORYSA | rice |
| Panicum dichotomiflorum | PANDI | fall panicum |
| Panicum milliaceum | PANMI | proso millet |
| Phalaris canariensis | PHACA | canarygrass |
| Ipomoea purpurea | PHBPU | tall morningglory |
| Poa annua | POAAN | annual bluegrass |
| Polygonum convolvulus | POLCO | wild buckwheat |
| Secale cereale | SECCW | winter rye |
| Setaria faberii | SETFA | giant foxtail |
| Setaria italica | SETIT | foxtail millet |
| Setaria lutescens | SETLU | yellow foxtail |
| Setaria viridis | SETVI | green foxtail |
| Solanum nigrum | SOLNI | black nightshade |
| Sorghum halepense | SORHA | johnsongrass |
| Stellaria media | STEME | chickweed |
| Thlaspi arvense | THLAR | field pennycress |
| Triticum aestivum | TRZAS | spring wheat |
| Triticum aestivum | TRZAW | winter wheat |
| Veronica persica | VERPE | field speedwell |
| Viola arvensis | VIOAR | field pansy |
| Xanthium strumarium | XANST | cocklebur |
| Zea mays | ZEAMX | corn |

The value E, which is to be expected if the activity of the individual compounds is just additive, was calculated using the method of S. R. Colby (1967) "Calculating synergistic and antagonistic responses of herbicide combinations", Weeds 15, p. 22 ff.

$$E = X + Y - (X \cdot Y/100)$$

where X=effect in percent using herbicide A at an application rate a;

Y=effect in percent using herbicide B at an application rate b;

E=expected effect (in %) of A+B at application rates a+b.

If the value observed in this manner is higher than the value E calculated according to Colby, a synergistic effect is present.

An accelerated activity is observed when the damage 8 days after treatment (8 DAT) achieved by the combination shows a synergistic effect.

Table 1a relates to the herbicidal activity of the individual actives in pre-emergence application assessed 8 DAT and 20 DAT. Table 1b relates the herbicidal activity of the combined actives in pre-emergence application assessed 8 DAT and 20 DAT.

Table 2a relates to the herbicidal activity of the individual actives in post-emergence application assessed 8 DAT and 20 DAT. Table 2b relates the herbicidal activity of the combined actives in post-emergence application assessed 8 DAT and 20 DAT.

Table 3 relates to the herbicidal activity of the individual actives and of the combinations in post-emergence application assessed 20 DAT.

TABLE 1a

Application in Pre-Emergence of pyroxasulfone and dicamba (individual activities)

| | pyroxasulfone (A) | | | dicamba (B) | | |
|---|---|---|---|---|---|---|
| | use rate | observed % activity | | use rate g ai/ha | observed % activity | |
| weed | [g ai/ha] | 8 DAT | 20 DAT | [g ai/ha] | 8 DAT | 20 DAT |
| ABUTH | 50 | 50 | 98 | 200 | 40 | 70 |
| ABUTH | 25 | 50 | 80 | 200 | 40 | 70 |
| AMBEL | 50 | 50 | 80 | 200 | 65 | 95 |
| HELAN | 25 | 0 | 0 | 200 | 75 | 85 |
| HELAN | 25 | 0 | 0 | 100 | 30 | 50 |
| HELAN | 50 | 0 | 0 | 50 | 30 | 35 |
| XANST | 25 | 0 | 0 | 200 | 85 | 95 |
| XANST | 25 | 0 | 0 | 100 | 50 | 80 |
| MATIN | 50 | 20 | 85 | 200 | 50 | 65 |

TABLE 1b

Application in Pre-Emergence of pyroxasulfone and dicamba (combined activities)

| | pyroxasulfone + dicamba | | | | | Synergism | |
|---|---|---|---|---|---|---|---|
| | use rate | Observed % activity | | expected % activity | | Y/N | Y/N |
| weed | [g ai/ha] | 8 DAT | 20 DAT | 8 DAT | 20 DAT | 8 DAT | 20 DAT |
| ABUTH | 50 + 200 | 90 | 100 | 70 | 99 | Y | Y |
| ABUTH | 25 + 200 | 90 | 100 | 70 | 94 | Y | Y |
| AMBEL | 50 + 200 | 90 | 100 | 83 | 99 | Y | Y |
| HELAN | 25 + 200 | 90 | 98 | 75 | 85 | Y | Y |
| HELAN | 25 + 100 | 50 | 85 | 30 | 50 | Y | Y |
| HELAN | 50 + 50 | 40 | 65 | 30 | 35 | Y | Y |
| XANST | 25 + 200 | 90 | 98 | 85 | 95 | Y | Y |
| XANST | 25 + 100 | 80 | 98 | 50 | 80 | Y | Y |
| MATIN | 50 + 200 | 75 | 98 | 60 | 95 | Y | Y |

TABLE 2a

Application in Post-Emergence of pyroxasulfone and dicamba (individual activities)

| | pyroxasulfone (A) | | | dicamba (B) | | |
|---|---|---|---|---|---|---|
| | use rate | observed % activity | | use rate g ai/ha | observed % activity | |
| weed | [g ai/ha] | 7 DAT | 20 DAT | [g ai/ha] | 7 DAT | 20 DAT |
| ECHCG | 13 | 25 | 80 | 100 | 20 | 15 |
| SETFA | 50 | 65 | 90 | 100 | 25 | 0 |
| SETFA | 50 | 65 | 90 | 50 | 25 | 0 |
| SETLU | 13 | 0 | 65 | 50 | 40 | 10 |
| ALOMY | 13 | 0 | 15 | 50 | 10 | 20 |

TABLE 2b

Application in Post-Emergence of pyroxasulfone and dicamba (combined activities)

| | | pyroxasulfone + dicamba | | | | Synergism | |
|---|---|---|---|---|---|---|---|
| | use rate | Observed % activity | | expected % activity | | Y/N | Y/N |
| weed | [g ai/ha] | 8 DAT | 20 DAT | 8 DAT | 20 DAT | 8 DAT | 20 DAT |
| ECHCG | 13 + 100 | 50 | 85 | 40 | 83 | Y | Y |
| SETFA | 50 + 100 | 80 | 95 | 74 | 90 | Y | Y |
| SETFA | 50 + 50 | 75 | 95 | 74 | 90 | Y | Y |
| SETLU | 13 + 50 | 55 | 80 | 40 | 69 | Y | Y |
| ALOMY | 13 + 50 | 20 | 35 | 10 | 32 | Y | Y |

TABLE 3

Application in Post-Emergence of pyroxasulfone and dicamba

| | pyroxasulfone (A) | | dicamba (B) | | pyroxasulfone + dicamba | | | |
|---|---|---|---|---|---|---|---|---|
| weed | use rate [g ai/ha] | 20 DAT[1] | use rate [g ai/ha] | 20 DAT[1] | use rate [g ai/ha] | 20 DAT[1] | 20 DAT[2] | Y/N[3] 20 DAT |
| PHBPU | 13 | 30 | 200 | 90 | 13 + 200 | 95 | 93 | Y |
| POLCO | 100 | 55 | 50 | 80 | 100 + 50 | 95 | 91 | Y |

1) observed activity in % destruction 20 days after treatment
2) calculated from the individual activities by Colby's formula
3) Synergism: Y = Yes; N = No

We claim:

1. A synergistic herbicidal composition comprising:
   a) a herbicide A which is 3-[5-(difluoromethoxy)-1-methyl-3-(trifluoromethyl)pyrazol-4-ylmethylsulfonyl]-4,5-dihydro-5,5-dimethyl-1,2-oxazole; and
   b) a herbicide B which is selected from the group consisting of dicamba, its salts and its esters,
   wherein the relative amount of herbicide A to herbicide B is 100:1 to 1:100.

2. The composition as claimed in claim 1, containing no safener.

3. An herbicide formulation comprising a composition as claimed in claim 1 and at least one solid or liquid carrier.

4. A method for controlling undesirable vegetation, comprising treating plants or their habitat with a composition as claimed in claim 1.

5. A method for controlling undesired vegetation, comprising applying a synergistic herbicidal composition comprising: a) a herbicide A which is 3-[5-(difluoromethoxy)-1-methyl-3-(trifluoromethyl)pyrazol-4-ylmethylsulfonyl]-4,5-dihydro-5,5-dimethyl-1,2-oxazole; and
b) a herbicide B which is selected from the group consisting of dicamba, its salts and its esters, before, during, and/or after the emergence of the undesirable plants; wherein the relative amount of herbicide A to herbicide B is 100:1 to 1:100.

* * * * *